United States Patent
Itoh et al.

(10) Patent No.: US 6,506,142 B2
(45) Date of Patent: Jan. 14, 2003

(54) HEALTH MAINTENANCE SYSTEM

(75) Inventors: Tomoya Itoh, Urawa (JP); Kazuhiko Arai, Urawa (JP)

(73) Assignee: Combi Corp., Tokyo (JP)

( * ) Notice: Subject to any disclaimer, the term of this patent is extended or adjusted under 35 U.S.C. 154(b) by 0 days.

(21) Appl. No.: 09/852,713

(22) Filed: May 11, 2001

(65) Prior Publication Data

US 2001/0041647 A1 Nov. 15, 2001

(30) Foreign Application Priority Data

May 11, 2000 (JP) ........................................ 2000-138560

(51) Int. Cl.$^7$ .............................................. A63B 21/00
(52) U.S. Cl. ............................................................ 482/8
(58) Field of Search ............................ 482/1–9, 51, 54, 482/57, 900–902

(56) References Cited

U.S. PATENT DOCUMENTS 4,907,795 A * 3/1990 Shaw et al. ..................... 482/9
5,716,330 A * 2/1998 Goldman ...................... 601/26
5,916,063 A * 6/1999 Alessandri ..................... 482/4

* cited by examiner

Primary Examiner—Glenn E. Richman
(74) Attorney, Agent, or Firm—Birch, Stewart, Kolasch & Birch, LLP

(57) ABSTRACT

A portable motion recorder (10) determines an amount of energy necessary for the daily basal metabolism of a user and the amount of energy consumed by the user for metabolism for living activities on the basis of measured data measured by a pedometer included therein and user's basic personal data entered by operating an input unit (12). Data provided by the portable motion recorder (10) is displayed on a display unit (16). The portable motion recorder (10) receives measured data measured by exercise machines (20, 30, 40) from the same. Comprehensive evaluation of energy consumed by the user is made on the basis of energy necessary for user's daily basal metabolism, energy consumed by the user for metabolism for living activities, and energy consumed by exercise using the exercise machines (20, 30, 40). The result of comprehensive evaluation as information about the user's health maintenance condition is displayed on the display unit (16).

17 Claims, 3 Drawing Sheets

HEALTH MAINTENANCE SYSTEM

BACKGROUND OF THE INVENTION

1. Field of the Invention

The present invention relates to a health maintenance system and, more particularly, to a health maintenance system using a portable motion recorder and exercise machines for general health maintenance.

2. Description of the Related Art

Counting the number of footsteps covered in a day by a portable motion recorder, such as a pedometer, and setting a desired number of footsteps to be covered in a day to practice a necessary amount of motion are practiced prevalently to supplement lack of exercise and to improve health. In addition to the forgoing daily activity, physical exercise using exercise machines, such as an ergometric exercise bicycle and a treadmill, is performed positively for fatness prevention and slimming.

Body fat ratio is an effective criterion for the discrimination between fatness and leanness. Values of fatness and leanness are dependent on basic personal data, such as sex, age, height, weight and the like. Therefore, basic personal data is an important criterion also.

There have been proposed portable motion recorders and exercise machines capable of indicating a necessary amount of exercise and a proper amount of caloric intake according to basic personal data and body fat ratio. Such motion recorders and exercise machines are provided with a basic personal data input device and a fat ratio measuring device and are capable of giving accurate desired values to the users of the portable motion recorders and the exercise machines.

Energy consumption of a person is the sum of energy for basal metabolism just enough to maintain vital functions and energy for metabolism for living activities. It is noted that "metabolism for living activities" means the physical and chemical processes excluding basal metabolism, which are produced in the person's body when the person does daily activity, such as walking. When the amount of caloric intake of a person is greater than the person's energy consumption, the person gains weight through lack of exercise. When the person exercises excessively, the energy consumption exceeds the amount of caloric intake.

The aforesaid portable motion recorder takes into consideration only the energy for basal metabolism and the energy for metabolism for living activities and does not take into consideration energy for exercise. The exercise machine counts only the energy consumed by exercise using the exercise machine and does not take into consideration the energy for basal metabolism and the energy for metabolism for living activities.

Therefore, it has been necessary for the comprehensive management of energy consumption to determine a necessary amount of exercise and a proper amount of caloric intake by processing information provided by the portable motion recorder and the exercise machine by a computer or the like.

SUMMARY OF THE INVENTION

The present invention has been made in view of the foregoing problems and it is therefore an object of the present invention to provide a health maintenance system capable of easily carrying out centralized comprehensive health maintenance using a portable motion recorder and exercise machines.

According to a first aspect of the present invention, a health maintenance system comprises: a portable motion recorder to be carried about by a user to measure the amount of motion for daily activities; and an exercise machine to be used in combination with the portable motion recorder, capable of providing the user with a predetermined exercise program and of measuring the amount of exercise performed by the user according to the exercise program; wherein the portable motion recorder and the exercise machine have communication functions for exchanging data, the portable motion recorder receives measured data from the exercise machine or the exercise machine receives measured data from the portable motion recorder through the communication functions, and the portable motion recorder received the measured data from the exercise machine or the exercise machine received the measured data from the portable motion recorder executes predetermined operations on the basis of the measured data measured by the portable motion recorder and the exercise machine and basic personal data on the user to provide information about health maintenance condition.

In this health maintenance system, it is preferable to store the basic personal data beforehand in the portable motion recorder when the same provides the information about health maintenance condition or in the exercise machine when the same provides the information about health maintenance condition. Preferably, the portable motion recorder receives the basic personal data together with the measured data through the communication functions from the exercise machine when the portable motion recorder provides the information about the health maintenance condition or the exercise machine receives the basic personal data together with the measured data through the communication functions from the portable motion recorder when the exercise machine provides the information about health maintenance condition. Preferably, the information about health maintenance condition includes at least either an amount of exercise necessary for the user or a proper amount of caloric intake. Preferably, the information about health maintenance condition further includes at least information about cardiopulmonary functions, information about physical composition, information about dynamic ability, the amount of exercise, the frequency of motions in a predetermined period or the amount of motion for daily activities.

According to a second aspect of the present invention, a portable motion recorder to be carried about by a user to measure the amount of motion for daily activities, and to be used in combination with an exercise machine that provides the user with a predetermined exercise program and measures the amount of exercise performed by the user according to the exercise program comprises: a motion measuring unit that measures the amount of motion for daily activities, a communication unit that exchanges data with the exercise machine; a data processing unit that receives measured data measured by the exercise machine from the exercise machine through the communication unit and processes measured data measured by the motion measuring unit, the measured data measured by and received from the exercise machine and basic personal data on the user by predetermined operations; and an output unit that provides information about health maintenance condition on the user determined by the data processing unit.

According to a third aspect of the present invention, an exercise machine capable of providing a user with a predetermined exercise program and of measuring the amount of exercise performed by the user according to the exercise program and to be used in combination with a portable motion recorder to be carried about by the user to measure the amount of motion for daily activities comprises: a motion measuring unit that measures the amount of exercise performed by the user according to the exercise program; a communication unit that exchanges data with the portable motion recorder; a data processing unit that receives measured data measured by the portable motion recorder from the portable motion recorder through the communication unit and processes measured data measured by the motion measuring unit, the measured data measured by and received from the portable motion recorder and basic personal data on the user by predetermined operations; and an output unit that provides information about health maintenance condition on the user determined by the data processing unit.

According to the present invention, the portable motion recorder and the exercise machine exchange data through the communication functions, the portable motion recorder receives measured data from the exercise machine or the exercise machine receives measured data from the portable motion recorder through the communication functions, the portable motion recorder and the exercise machine process the measured data measured by the portable motion recorder and the exercise machine and the basic personal data by the predetermined calculating operations to provide the user with information about health maintenance condition. Thus a complicated work for applying the information provided by the portable motion recorder and the exercise machine to an external computer or the like is unnecessary and all the data on energy for basal metabolism, energy for metabolism for living activities and energy consumption by the exercise using the exercise machine, so that comprehensive, centralized health maintenance management can be easily achieved.

BRIEF DESCRIPTION OF THE DRAWINGS

Preferred embodiments of the present invention will be described with reference to the accompanying drawings, in which.

DESCRIPTION OF THE PREFERRED EMBODIEMNTS

Figure 1:
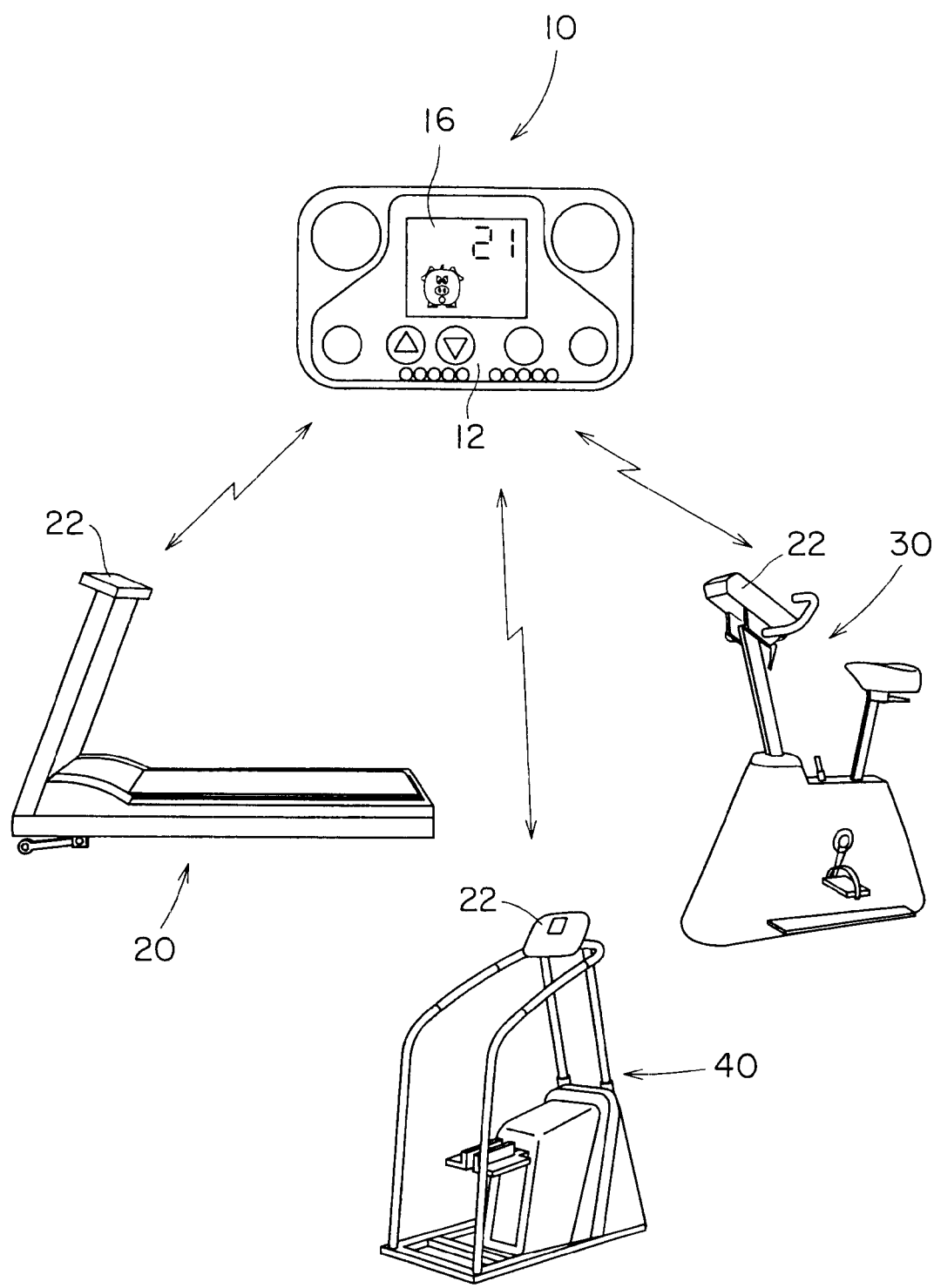
FIG. 1 is a pictorial view of a health maintenance system in a preferred embodiment of the present invention.

Referring to FIG. 1, a health maintenance system in a preferred embodiment of the present invention includes a portable motion recorder 10 to be fastened to the body of a user with a band, not shown, or the like, and exercise machines 20, 30 and 40 used in combination with the portable motion recorder.

Figure 2:
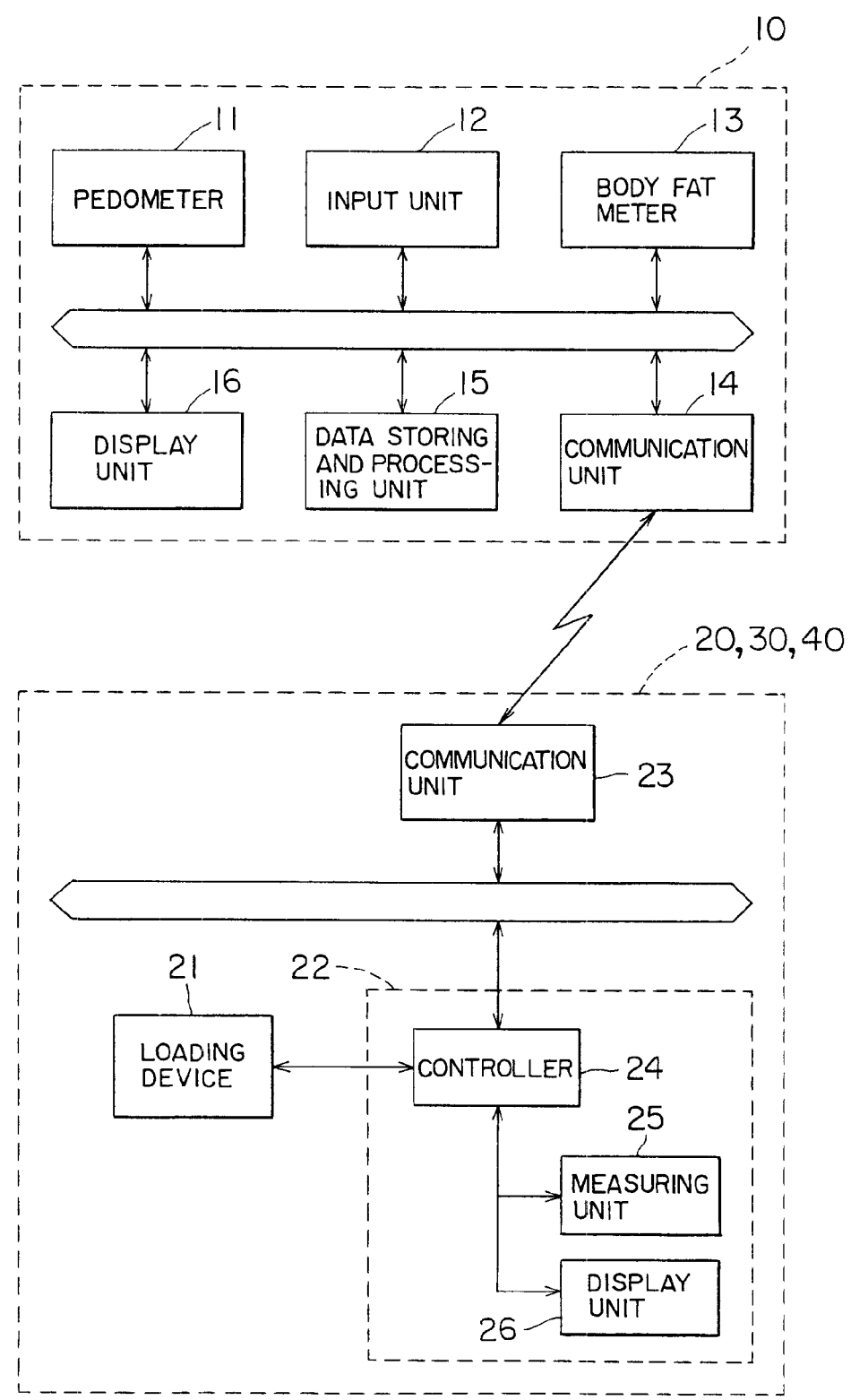
FIG. 2 is a block diagram of the health maintenance system shown in FIG. 1.

The portable motion recorder 10 measures the amount of user's motion for daily activities. As shown in FIGS. 1 and 2, the portable motion recorder 10 includes a pedometer (motion measuring device) 11 for counting the number of user's footsteps (amount of motion), an input unit 12 to be operated to enter user's basic personal data including sex, age, height and weight, and a body fat meter 13 for measuring user's body fat ratio. The portable motion recorder 10 further includes a communication unit 14 that exchanges data with the exercise machines 20, 30 and 40, a data storing and processing unit 15 that stores measured data, basic personal data, the body fat ratio and such and determines user's health maintenance condition, a display unit (output unit) 16 that displays user's health maintenance condition determined by the data storing and processing unit 15. The portable motion recorder 10 may include other measuring devices including a weighing device for measuring user's weight, which is one of the basic personal data.

Concretely, the exercise machines 20, 30 and 40 are a treadmill, an ergometric exercise bicycle and a step machine, respectively, which are used in homes and sport facilities. The exercise machines 20, 30 and 40 provide users with exercise programs and measure the amount of motion according to the exercise programs. As shown in FIGS. 1 and 2, each of the exercise machines 20, 30 and 40 is provided with a loading device 21 that applies a predetermined load to the user, a control unit 22 that controls the loading device 21 according to instructions given thereto by the user, and a communication unit 23 that exchanges data with the portable motion recorder 10. As shown in FIG. 1, the control unit 22 is disposed on the casing of each of the exercise machines 20, 30 and 40 so that the user may be able to operate the same.

The control unit 22 includes a controller 24 for controlling the loading device 21, a measuring unit 25 for measuring the amount of user's motion according to the predetermined exercise program, and a display unit 26 for displaying the amount of user's motion measured by the measuring unit 25. The amount of user's motion displayed on the display unit 26 includes a distance covered by the user, user's moving speeds, the number of user's footsteps and the amount of energy consumed by motion.

Functions of the health maintenance system thus constructed will be described hereinafter.

The user bears the portable motion recorder 10 during daily life. The pedometer 11 of the portable motion recorder 10 counts the number of footsteps or a distance covered by the user in a day. Measurements provided by the pedometer 11 are displayed on the screen of the display unit 16.

The data storing and processing unit 15 of the portable motion recorder 10 calculates the amount of energy consumed in a day by user's basal metabolism, the amount of energy consumed by user's living activities or the ratio of the amount of energy consumed to that of energy taken in on the basis of measured data including the number of user's footsteps, provided by the pedometer 11, the user's basic personal data entered by operating the input unit 12, and the user's body fat ratio measured by the body fat meter 13. Data thus calculated is displayed on the display unit 16.

The data storing and processing unit 15 of the portable motion recorder 10 receives measured data including a distance covered by the user, user's moving speed, the number of steps and the amount of energy consumed by exercise measured by the exercise machines 20, 30 and 40 from the exercise machines 20, 30 and 40 through the communication unit 14. The amount of energy consumed by exercise using the exercise machines 20, 30 and 40 is added to the sum of the aforesaid amount of energy consumed in a day by user's basal metabolism and the amount of energy consumed by user's living activities. The user's energy consumption is evaluated comprehensively and the results of comprehensive evaluation indicating user's health maintenance condition are displayed selectively on the display unit 16.

Figure 3:
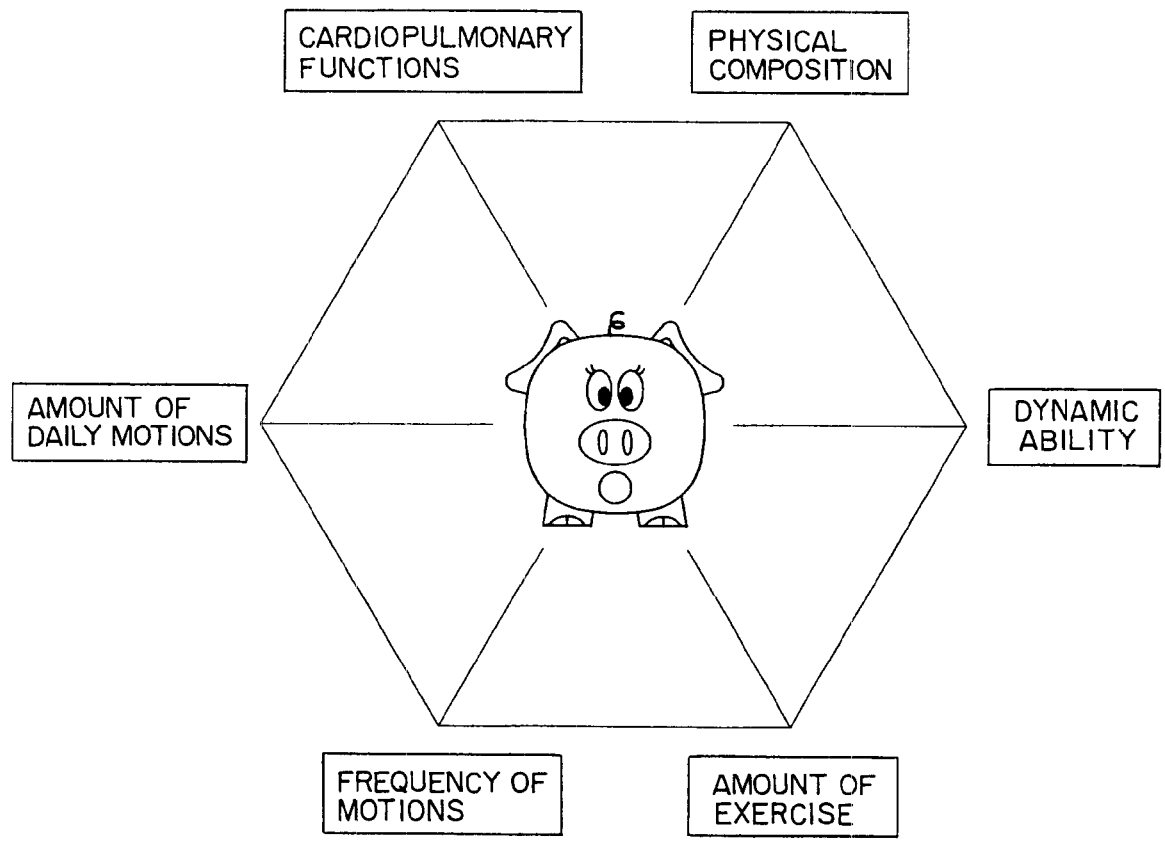
FIG. 3 is a view of a picture displayed on the screen of a monitor included in a portable motion recorder included in the health maintenance system shown in FIG. 1.

Data to be displayed on the display unit 16 may include the total amount of consumed energy, the ratio of the total amount of consumed energy to the amount of energy taken in, a amount of exercise necessary for the user and an amount of energy that may be taken in by the user. The user's health maintenance condition may be represented by cardiopulmonary functions, physical composition, dynamic ability, the amount of exercise, the frequency of motions in a predetermined period and the amount of daily motions in a graph as shown in FIG. 3 to enable the evaluation of the quality and amount of exercise. The development of the effect of exercise may be expressed by the variation of the morphology of a cartoon character to enjoy the process of daily activities and exercise using the exercise machines.

The portable motion recorder 10 and the exercise machines 20, 30 and 40 are able to exchange data through the communication units 14 and 23, the data storing and processing unit 15 of the portable motion recorder 10 accumulates measured data measured by the pedometer 11, measured data measured by and received from the exercise machines 20, 30 and 40, the user's basic personal data and the user's body fat ratio, and executes predetermined operations to processes the accumulated data to provide information about the user's health maintenance condition, and the display unit 16 displays the information about the user's health maintenance condition. Therefore, the total amount of energy consumed by basal metabolism, metabolism for living activities and exercise using the exercise machines 20, 30 and 40 can be controlled without requiring troublesome work for applying data provided by the portable motion recorder 10 and the exercise machines 20, 30 and 40 to an external computer or the like. Thus, comprehensive health maintenance can be easily achieved.

Measured data measured by the exercise machines 20, 30 and 40 is given to the portable motion recorder 10 as required. Thus the portable motion recorder 10 can collectively control all the measured data even if the exercise machines 20, 30 and 40 are used in sequence. The portable motion recorder 10 can be used as a personal terminal device exclusively for the user and the comprehensive heal maintenance can be achieved by the single personal terminal device.

The communication unit 14 of the portable motion recorder 10 and the communication units 23 of the exercise machines 20, 30 and 40 may be of any one of a wire system, a wireless system and a contact system.

The user's basic personal data does not need necessarily to be entered beforehand into the portable motion recorder 10 by operating the input unit 13; the user's basic personal data may be given together with measured data measured by the exercise machines 20, 30 and 40.

Although the portable motion recorder 10 receives the measured data from the exercise machines 20, 30 and 40 and provides the user with the information about the health maintenance condition in the foregoing embodiment, the exercise machines 20, 30 and 40 may receive the measured data measured by the portable motion recorder 10 from the portable motion recorder 10 and provide the user with the information about the health maintenance condition. In the latter case, the controllers (storing and processing units) 24 of the control units 22 receive the measured data measured by the portable motion recorder 10 from the portable motion recorder 10 through the communication units 23 and executes predetermined operations on the basis of the measured data obtained by the measuring units 25, the measured data measured by and received from the portable motion recorder 10, the user's basic personal data and the user's body fat ratio. Thus the controllers 24 determine data on the user's health maintenance condition and the display units (output units) 26 display the data on the user's health maintenance condition. The controllers 24 receive the user's basic personal data and the user's body fat ratio through the communication units 23 from the portable motion recorder 10.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A health maintenance system comprising:
    a portable motion recorder including a motion measuring unit to be carried about by a user to measure an amount of motion for daily activities; and
    an exercise machine to be used in combination with the portable motion recorder, capable of providing the user with a predetermined exercise program and of measuring an amount of exercise performed by the user according to the exercise program;
    wherein the portable motion recorder and the exercise machine have communication functions for exchanging data, the portable motion recorder receives measured data from the: exercise machine or the exercise machine receives measured data from the portable motion recorder through the communication functions, and the portable motion recorder received the measured data from the exercise machine or the exercise machine received the measured data from the portable motion recorder executes predetermined operations on the basis of the measured data measured by the portable motion recorder and the exercise machine and basic personal data on the user to provide information about health maintenance condition.

2. The health maintenance system according to claim 1, wherein the basic personal data is stored beforehand in the portable motion recorder when the same provides the information about health maintenance condition or in the exercise machine when the same provides the information about health maintenance condition.

3. The health maintenance system according to claim 1, wherein the portable motion recorder receives the basic personal data together with the measured data through the communication functions from the exercise machine when the portable motion recorder provides the information about health maintenance condition or the exercise machine receives the basic personal data together with the measured data through the communication functions from the portable motion recorder when the exercise machine provides the information about health maintenance condition.

4. The health maintenance system according to claim 1, wherein the information about health maintenance condition includes at least either an amount of exercise necessary for the user or a proper amount of caloric intake.

5. The health maintenance system according to claim 4, wherein the information about health maintenance condition further includes at least information about cardiopulmonary functions, information about physical composition, information about dynamic ability, an amount of exercise, a frequency of motions in a predetermined period or an amount of motion for daily activities.

6. A portable motion recorder to be carried about by a user to measure an amount of motion for daily activities, and to be used in combination with an exercise machine that provides the user with a predetermined exercise program and measures an amount of exercise performed by the user according to the exercise program, said portable motion recorder comprising:

a motion measuring unit that measures an amount of motion for daily activities;

a communication unit that exchanges data with the exercise machine;

a data processing unit that receives measured data measured by the exercise machine from the exercise machine through the communication unit and processes measured data measured by the motion measuring unit, the measured data measured by and received from the exercise machine and basic personal data on the user by predetermined operations; and an output unit that provides information about health maintenance condition on the user determined by the data processing unit.

7. The portable motion recorder according to claim 6, further comprising an input unit for entering the basic personal data on the user.

8. The portable motion recorder according to claim 6, further comprising a body fat meter for measuring body fat ratio on the user; wherein the data processing unit processes the body fat ratio measured by the body fat meter together with the basic personal data by the predetermined operations.

9. The portable motion recorder according to claim 6, wherein the motion measuring unit is a pedometer that counts the number of footsteps stepped by the user.

10. The portable motion recorder according to claim 6, wherein the information about health maintenance condition on the user provided by the output unit includes at least either an amount of motion necessary for the user or a proper amount of caloric intake.

11. The portable motion recorder according to claim 10, wherein the information about health maintenance condition on the user further includes at least information about cardiopulmonary functions, information about physical composition, information about dynamic ability, an amount of exercise, a frequency of motions in a predetermined period or an amount of motion for daily activities.

12. An exercise machine capable of providing a user with a predetermined exercise program and of measuring an amount of exercise performed by the user according to the exercise program and to be used in combination with a portable motion recorder to be carried about by the user to measure an amount of motion for daily activities, said exercise machine comprising:

a motion measuring unit that measures an amount of exercise performed by the user according to the exercise program;

a communication unit that exchanges data with the portable motion recorder;

a data processing unit that receives measured data measured by the portable motion recorder from the portable motion recorder through the communication unit and processes measured data measured by the motion measuring unit, the measured data measured by and received from the portable motion recorder and basic personal data on the user by predetermined operations; and an output unit that provides information about health maintenance condition on the user determined by the data processing unit.

13. The exercise machine according to claim 12, wherein the basic personal data is received through the communication unit from the portable motion recorder.

14. The exercise machine according to claim 12, a body fat ratio measured by the portable motion recorder is received together with the basic personal data through the communication unit from the portable motion recorder, the data processing unit processes the body fat ratio together with the basic personal data by the predetermined operations.

15. The exercise machine according to claim 12, wherein the mount of motion measured by the portable motion recorder is the number of footsteps stepped by the user.

16. The exercise machine according to claim 12, wherein the information about health maintenance condition on the user provided by the output unit includes at least either an amount of motion necessary for the user or a proper amount of caloric intake.

17. The exercise machine according to claim 16, wherein the information about health maintenance condition on the user further includes at least information about cardiopulmonary functions, information about physical composition, information about dynamic ability, an amount of exercise, a frequency of motions in a predetermined period or an amount of motion for daily activities.

* * * * *